(12) United States Patent
Williams et al.

(10) Patent No.: US 8,771,334 B2
(45) Date of Patent: ***Jul. 8, 2014

(54) CATHETER BALLOON SYSTEMS AND METHODS

(75) Inventors: Eric Williams, Fairfield, CA (US);
Daryush Mirzaee, Sunnyvale, CA (US);
Michael Khenansho, Modesto, CA (US); Michael Schwartz, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 404 days.

This patent is subject to a terminal disclaimer.

(21) Appl. No.: 12/638,614

(22) Filed: Dec. 15, 2009

(65) Prior Publication Data

US 2010/0087909 A1    Apr. 8, 2010

Related U.S. Application Data

(63) Continuation of application No. 10/834,066, filed on Apr. 29, 2004, now Pat. No. 7,655,030.

(60) Provisional application No. 60/548,868, filed on Mar. 2, 2004, provisional application No. 60/547,778, filed on Feb. 27, 2004, provisional application No. 60/518,870, filed on Nov. 12, 2003, provisional application No. 60/488,006, filed on Jul. 18, 2003.

(51) Int. Cl.
*A61F 2/954*    (2013.01)

(52) U.S. Cl.
USPC .............. 623/1.11; 604/101.04; 623/1.35

(58) Field of Classification Search
CPC ............. A61F 2/07; A61F 2/95; A61F 2/954; A61F 2/958; A61F 2002/82–2002/96; A61F 2002/9517; A61F 2002/958; A61F 2002/9583; A61M 2025/1045; A61M 2025/1072
USPC .......................... 606/191–200; 623/1.11–1.54; 604/101.01–101.05, 103.06–103.08
See application file for complete search history.

(56) References Cited

U.S. PATENT DOCUMENTS

| | | | |
|---|---|---|---|
| 1,596,754 A | 8/1926 | Moschelle |
| 3,657,744 A | 4/1972 | Ersek |

(Continued)

FOREIGN PATENT DOCUMENTS

| | | |
|---|---|---|
| CA | 2318314 | 7/1999 |
| DE | 90 14 845.2 | 2/1991 |

(Continued)

OTHER PUBLICATIONS

Caputo, Ronald P. et al., "Stent Jail: A Minimum-Security Prision," *The American Journal of Cardiology*, vol. 7 (1996) pp. 1226-1230.

(Continued)

*Primary Examiner* — Kathleen Holwerda
(74) *Attorney, Agent, or Firm* — Seager, Tufte & Wickhem LLC

(57) ABSTRACT

An apparatus for treatment of a bifurcation of a body lumen, the bifurcation having a main vessel and a branch vessel, the apparatus includes a bifurcated balloon with a first branch portion and a second branch portion, the second branch portion including an inflatable portion adapted to extend toward the branch vessel, the bifurcated balloon also having a proximal shaft portion and a distal shaft portion connected to the inflatable portion of the second branch portion, and wherein the first branch portion and the second branch portion each have a longitudinal axis, the axis of the first branch portion being substantially parallel to the longitudinal axis of the second branch portion.

20 Claims, 10 Drawing Sheets

(56) References Cited

U.S. PATENT DOCUMENTS

| | | | |
|---|---|---|---|
| 3,872,893 | A | 3/1975 | Roberts |
| 4,140,126 | A | 2/1979 | Choudhury |
| 4,309,994 | A | 1/1982 | Grunwald |
| 4,410,476 | A | 10/1983 | Redding et al. |
| 4,413,989 | A | 11/1983 | Schjeldahl |
| 4,421,810 | A | 12/1983 | Rasmussen |
| 4,453,545 | A | 6/1984 | Inoue |
| 4,503,569 | A | 3/1985 | Dotter |
| 4,552,554 | A | 11/1985 | Gould et al. |
| 4,681,570 | A | 7/1987 | Dalton |
| 4,689,174 | A | 8/1987 | Lupke |
| 4,731,055 | A | 3/1988 | Melnyshyn et al. |
| 4,733,665 | A | 3/1988 | Palmaz |
| 4,739,762 | A | 4/1988 | Palmaz |
| 4,759,748 | A | 7/1988 | Reed |
| 4,762,128 | A | 8/1988 | Rosenbluth |
| 4,769,029 | A | 9/1988 | Patel |
| 4,819,664 | A | 4/1989 | Nazari |
| 4,872,874 | A | 10/1989 | Taheri |
| 4,878,495 | A | 11/1989 | Grayzel |
| 4,896,670 | A | 1/1990 | Crittenden |
| 4,900,314 | A | 2/1990 | Quackenbush |
| 4,906,244 | A | 3/1990 | Pinchuk et al. |
| 4,909,258 | A | 3/1990 | Kuntz et al. |
| 4,946,464 | A | 8/1990 | Pevsner |
| 4,957,501 | A | 9/1990 | Lahille et al. |
| 4,957,508 | A | 9/1990 | Kaneko et al. |
| 4,964,850 | A | 10/1990 | Bouton et al. |
| 4,983,167 | A | 1/1991 | Sahote |
| 4,994,071 | A | 2/1991 | MacGregor |
| 5,042,976 | A | 8/1991 | Ishitsu et al. |
| 5,054,501 | A | 10/1991 | Chuttani et al. |
| 5,059,177 | A | 10/1991 | Towne et al. |
| 5,061,240 | A | 10/1991 | Cherian |
| 5,064,435 | A | 11/1991 | Porter |
| 5,085,664 | A | 2/1992 | Bozzo |
| 5,102,403 | A | 4/1992 | Alt |
| 5,102,417 | A | 4/1992 | Palmaz |
| 5,104,404 | A | 4/1992 | Wolff |
| 5,117,831 | A | 6/1992 | Jang |
| 5,122,125 | A | 6/1992 | Deuss |
| 5,135,536 | A | 8/1992 | Hillstead |
| 5,147,317 | A | 9/1992 | Shank et al. |
| 5,147,385 | A | 9/1992 | Beck et al. |
| 5,159,920 | A | 11/1992 | Condon et al. |
| 5,176,617 | A | 1/1993 | Fischell et al. |
| 5,192,297 | A | 3/1993 | Hull |
| 5,195,984 | A | 3/1993 | Schatz |
| 5,211,683 | A | 5/1993 | Maginot |
| 5,217,440 | A | 6/1993 | Frassica |
| 5,222,971 | A | 6/1993 | Willard et al. |
| 5,226,913 | A | 7/1993 | Pinchuk |
| 5,234,457 | A | 8/1993 | Anderssen |
| 5,236,446 | A | 8/1993 | Dumon |
| 5,257,974 | A | 11/1993 | Cox |
| 5,263,932 | A | 11/1993 | Jang |
| 5,282,472 | A | 2/1994 | Companion et al. |
| 5,304,220 | A | 4/1994 | Maginot |
| 5,320,605 | A | 6/1994 | Sahota |
| 5,324,257 | A | 6/1994 | Osborne et al. |
| 5,337,733 | A | 8/1994 | Bauerfeind et al. |
| 5,338,300 | A | 8/1994 | Cox |
| 5,342,295 | A | 8/1994 | Imran |
| 5,342,297 | A | 8/1994 | Jang |
| 5,342,387 | A | 8/1994 | Summers |
| 5,350,395 | A | 9/1994 | Yock |
| 5,383,856 | A | 1/1995 | Bersin |
| 5,383,892 | A | 1/1995 | Cardon et al. |
| 5,387,235 | A | 2/1995 | Chuter |
| 5,395,332 | A | 3/1995 | Ressemann et al. |
| 5,395,334 | A | 3/1995 | Keith et al. |
| 5,404,887 | A | 4/1995 | Prather |
| 5,409,458 | A | 4/1995 | Khairkhahan et al. |
| 5,413,581 | A | 5/1995 | Goy |
| 5,413,586 | A | 5/1995 | Dibie et al. |
| 5,417,208 | A | 5/1995 | Winkler |
| 5,425,765 | A | 6/1995 | Tiefenbrun et al. |
| 5,437,638 | A | 8/1995 | Bowman |
| 5,443,497 | A | 8/1995 | Venbrux |
| 5,445,624 | A | 8/1995 | Jimenez |
| 5,449,373 | A | 9/1995 | Pinchasik et al. |
| 5,449,382 | A | 9/1995 | Dayton |
| 5,456,694 | A | 10/1995 | Marin et al. |
| 5,456,712 | A | 10/1995 | Maginot |
| 5,456,714 | A | 10/1995 | Owen |
| 5,458,605 | A | 10/1995 | Klemm |
| 5,462,530 | A | 10/1995 | Jang |
| 5,476,471 | A | 12/1995 | Shifrin et al. |
| 5,489,271 | A | 2/1996 | Anderson |
| 5,489,295 | A | 2/1996 | Piplani et al. |
| 5,496,292 | A | 3/1996 | Burnham |
| 5,505,702 | A * | 4/1996 | Arney ............... 604/101.01 |
| 5,507,768 | A | 4/1996 | Lau et al. |
| 5,507,769 | A | 4/1996 | Marin et al. |
| 5,514,154 | A | 5/1996 | Lau et al. |
| 5,514,178 | A | 5/1996 | Torchio |
| 5,522,801 | A | 6/1996 | Wang |
| 5,531,788 | A | 7/1996 | Dibie et al. |
| 5,545,132 | A | 8/1996 | Fagan et al. |
| 5,549,553 | A | 8/1996 | Ressemann et al. |
| 5,549,554 | A | 8/1996 | Miraki |
| 5,549,555 | A * | 8/1996 | Sohn ............... 604/101.01 |
| 5,562,620 | A | 10/1996 | Klein et al. |
| 5,562,724 | A | 10/1996 | Vorwerk et al. |
| 5,562,725 | A | 10/1996 | Schmitt et al. |
| 5,562,726 | A | 10/1996 | Chuter |
| 5,569,295 | A | 10/1996 | Lam |
| 5,571,087 | A | 11/1996 | Ressemann et al. |
| 5,575,771 | A | 11/1996 | Walinsky |
| 5,575,817 | A | 11/1996 | Martin |
| 5,575,818 | A | 11/1996 | Pinchuk |
| 5,591,228 | A | 1/1997 | Edoga |
| 5,593,442 | A | 1/1997 | Klein |
| 5,607,444 | A | 3/1997 | Lam |
| 5,609,625 | A | 3/1997 | Piplani et al. |
| 5,609,627 | A | 3/1997 | Goicoechea et al. |
| 5,609,629 | A | 3/1997 | Fearnot et al. |
| 5,613,949 | A | 3/1997 | Miraki |
| 5,613,980 | A | 3/1997 | Chauhan |
| 5,613,981 | A | 3/1997 | Boyle et al. |
| 5,617,878 | A | 4/1997 | Taheri |
| 5,626,600 | A | 5/1997 | Horzewski et al. |
| 5,628,788 | A | 5/1997 | Pinchuk |
| 5,632,762 | A | 5/1997 | Myler |
| 5,632,763 | A | 5/1997 | Glastra |
| 5,632,772 | A | 5/1997 | Alcime et al. |
| 5,634,902 | A | 6/1997 | Johnson et al. |
| 5,639,278 | A | 6/1997 | Dereume et al. |
| 5,643,340 | A | 7/1997 | Nunokawa |
| 5,653,743 | A | 8/1997 | Martin |
| 5,662,614 | A | 9/1997 | Edoga |
| 5,669,924 | A | 9/1997 | Shaknovish |
| 5,669,932 | A | 9/1997 | Fischell et al. |
| 5,676,696 | A | 10/1997 | Marcade |
| 5,676,697 | A | 10/1997 | McDonald |
| 5,679,400 | A | 10/1997 | Tuch |
| 5,683,451 | A | 11/1997 | Lenker et al. |
| 5,690,642 | A | 11/1997 | Osborne et al. |
| 5,693,084 | A | 12/1997 | Chuter |
| 5,693,086 | A | 12/1997 | Goicoechea et al. |
| 5,693,088 | A | 12/1997 | Lazarus |
| 5,697,971 | A | 12/1997 | Fischell et al. |
| 5,707,354 | A | 1/1998 | Salmon et al. |
| 5,709,713 | A | 1/1998 | Evans et al. |
| 5,716,365 | A | 2/1998 | Goicoechea et al. |
| 5,718,683 | A | 2/1998 | Ressemann et al. |
| 5,718,724 | A | 2/1998 | Goicoechea et al. |
| 5,720,735 | A | 2/1998 | Dorros |
| 5,723,004 | A | 3/1998 | Dereume et al. |
| 5,724,977 | A | 3/1998 | Yock et al. |
| 5,728,158 | A | 3/1998 | Lau et al. |
| 5,733,303 | A | 3/1998 | Israel et al. |
| 5,735,893 | A | 4/1998 | Lau et al. |
| 5,746,766 | A | 5/1998 | Edoga |

(56) References Cited

U.S. PATENT DOCUMENTS

| | | |
|---|---|---|
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | von Oepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,193,747 B1 | 2/2001 | von Oepen |
| 6,203,569 B1 | 3/2001 | Wijay |
| 6,210,380 B1 | 4/2001 | Mauch |
| 6,210,429 B1 | 4/2001 | Vardi |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Ehr et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,570 B1 | 8/2002 | Globerman |
| 6,432,133 B1 | 8/2002 | Lau et al. |
| 6,436,104 B2 | 8/2002 | Hojeibane |
| 6,436,134 B2 | 8/2002 | Richter et al. |
| 6,478,816 B1 | 11/2002 | Kveen et al. |
| 6,482,211 B1 | 11/2002 | Choi |
| 6,485,511 B2 | 11/2002 | Lau et al. |
| 6,494,905 B1 | 12/2002 | Zedler et al. |
| 6,511,504 B1 | 1/2003 | Lau et al. |
| 6,511,505 B2 | 1/2003 | Cox et al. |
| 6,520,988 B1 | 2/2003 | Colombo et al. |
| 6,527,799 B2 | 3/2003 | Shanley |
| 6,540,719 B2 | 4/2003 | Bigux et al. |
| 6,540,779 B2 | 4/2003 | Richter et al. |
| 6,572,647 B1 | 6/2003 | Supper et al. |
| 6,579,309 B1 | 6/2003 | Loos et al. |

(56) References Cited

U.S. PATENT DOCUMENTS

| | | |
|---|---|---|
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,022 B2 | 7/2003 | Lau et al. |
| 6,599,316 B2 | 7/2003 | Vardi et al. |
| 6,645,241 B1 | 11/2003 | Strecker |
| 6,676,691 B1 * | 1/2004 | Hosny ............ 623/1.11 |
| 6,689,156 B1 | 2/2004 | Davidson et al. |
| 6,692,483 B2 | 2/2004 | Vardi et al. |
| 6,706,062 B2 | 3/2004 | Vardi et al. |
| 6,709,440 B2 * | 3/2004 | Callol et al. ............ 606/108 |
| 6,719,720 B1 | 4/2004 | Voelker et al. |
| 7,655,030 B2 * | 2/2010 | Williams et al. ......... 623/1.11 |
| 2001/0012927 A1 | 8/2001 | Mauch |
| 2001/0016767 A1 | 8/2001 | Wilson et al. |
| 2001/0016768 A1 | 8/2001 | Wilson et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0037146 A1 | 11/2001 | Lau et al. |
| 2001/0037147 A1 | 11/2001 | Lau et al. |
| 2001/0039395 A1 | 11/2001 | Mareiro et al. |
| 2001/0039448 A1 | 11/2001 | Debie |
| 2001/0047201 A1 | 11/2001 | Cox et al. |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0032478 A1 | 3/2002 | Boekstegers et al. |
| 2002/0035392 A1 | 3/2002 | Wilson |
| 2002/0042650 A1 | 4/2002 | Vardi et al. |
| 2002/0052648 A1 | 5/2002 | McGuckin et al. |
| 2002/0058990 A1 | 5/2002 | Jang |
| 2002/0072790 A1 | 6/2002 | McGuckin et al. |
| 2002/0107564 A1 | 8/2002 | Cox et al. |
| 2002/0111675 A1 | 8/2002 | Wilson |
| 2002/0120233 A1 | 8/2002 | Eidenschink et al. |
| 2002/0123790 A1 | 9/2002 | White et al. |
| 2002/0123797 A1 | 9/2002 | Majercak |
| 2002/0123798 A1 | 9/2002 | Burgermeister |
| 2002/0151959 A1 | 10/2002 | von Oepen |
| 2002/0156516 A1 | 10/2002 | Vardi et al. |
| 2002/0156517 A1 | 10/2002 | Perouse |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0177892 A1 | 11/2002 | Globerman |
| 2002/0183763 A1 * | 12/2002 | Callol et al. ............ 606/108 |
| 2002/0193872 A1 | 12/2002 | Trout et al. |
| 2002/0193873 A1 | 12/2002 | Brucker et al. |
| 2003/0004535 A1 | 1/2003 | Musbach et al. |
| 2003/0009209 A1 | 1/2003 | Hojeibane |
| 2003/0009214 A1 | 1/2003 | Shanley |
| 2003/0014102 A1 | 1/2003 | Hong et al. |
| 2003/0023301 A1 | 1/2003 | Cox et al. |
| 2003/0028211 A1 | 2/2003 | Crocker et al. |
| 2003/0050688 A1 | 3/2003 | Fischell et al. |
| 2003/0074047 A1 | 4/2003 | Richter |
| 2003/0093109 A1 | 5/2003 | Mauch |
| 2003/0114912 A1 | 6/2003 | Sequin et al. |
| 2003/0114915 A1 | 6/2003 | Mareiro et al. |
| 2003/0125791 A1 | 7/2003 | Sequin et al. |
| 2003/0125799 A1 | 7/2003 | Limon et al. |
| 2003/0125802 A1 | 7/2003 | Callol et al. |
| 2003/0167083 A1 | 9/2003 | Lashinski et al. |
| 2003/0181923 A1 | 9/2003 | Vardi |
| 2004/0015227 A1 | 1/2004 | Vardi et al. |
| 2004/0049259 A1 | 3/2004 | Strecker |
| 2004/0072849 A1 | 4/2004 | Schreiber et al. |
| 2004/0133268 A1 | 7/2004 | Davidson et al. |
| 2004/0138737 A1 | 7/2004 | Davidson et al. |
| 2004/0148006 A1 | 7/2004 | Davidson et al. |
| 2008/0208307 A1 * | 8/2008 | Ben-Muvhar et al. ....... 623/1.11 |

FOREIGN PATENT DOCUMENTS

| | | |
|---|---|---|
| DE | 297 01 758 | 5/1997 |
| EP | 0 551 179 | 7/1993 |
| EP | 0 646 365 | 4/1995 |
| EP | 0 684 022 | 11/1995 |
| EP | 0 804 907 | 11/1997 |
| EP | 0 876 805 | 11/1998 |
| EP | 0 884 028 | 12/1998 |
| EP | 0 891 751 | 1/1999 |
| EP | 0 897 698 | 2/1999 |
| EP | 0 897 700 | 2/1999 |
| EP | 0 904 745 | 3/1999 |
| EP | 1 031 328 | 8/2000 |
| EP | 1 031 330 | 8/2000 |
| EP | 1 157 674 | 11/2001 |
| EP | 1 254 644 | 11/2002 |
| FR | 2 678 508 | 1/1993 |
| WO | WO 88/06026 | 8/1988 |
| WO | WO 90/13332 | 11/1990 |
| WO | WO 91/12779 | 9/1991 |
| WO | 92/14507 A1 | 9/1992 |
| WO | WO 92/19308 | 11/1992 |
| WO | WO 95/08965 | 4/1995 |
| WO | WO 95/21592 | 8/1995 |
| WO | WO 96/29955 | 10/1996 |
| WO | WO 96/41592 | 12/1996 |
| WO | WO 97-09946 | 3/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 98/17204 | 4/1998 |
| WO | WO 98/19628 | 5/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/48733 | 11/1998 |
| WO | WO 98/52497 | 11/1998 |
| WO | WO 99/00835 | 1/1999 |
| WO | WO 99/15103 | 4/1999 |
| WO | WO 99/17680 | 4/1999 |
| WO | WO 99/24104 | 5/1999 |
| WO | WO 99/34749 | 7/1999 |
| WO | WO 99/36002 | 7/1999 |
| WO | WO 99/39661 | 8/1999 |
| WO | WO 99/58059 | 11/1999 |
| WO | WO 99/65419 | 12/1999 |
| WO | WO 00/00104 | 1/2000 |
| WO | WO 00/12166 | 3/2000 |
| WO | WO 00/13613 | 3/2000 |
| WO | WO 00/53122 | 9/2000 |
| WO | 00/74595 A1 | 12/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/068012 | 9/2002 |
| WO | WO 02/076333 | 10/2002 |
| WO | WO 02/094336 | 11/2002 |
| WO | WO 03/055414 | 7/2003 |
| WO | WO 2004/026180 | 4/2004 |
| WO | 2005/041810 A2 | 5/2005 |
| WO | WO 2005/046757 | 5/2005 |

OTHER PUBLICATIONS

Carrie, Didier et al., "'T'-Shaped Stent Placement: A Technique for the Treatment of Dissected Bifurcation Lesions," *Catheterization and Cardiovascular Diagnosis*, vol. 37 (1996) pp. 311-313.

(56) References Cited

OTHER PUBLICATIONS

Chevalier, Bernard et al., "Placement of Coronary Stents in Bifurcation Lesions by the 'Coulotte' Technique," *American Journal of Cardiology*, vol. 82, Oct. 15, 1998, pp. 943-949.

Colombo, Antonio et al., "'Kissing' Stents for Bifurcational Coronary Lesion," *Catheterization and Cardiovascular Diagnosis*, vol. 30 (1993) pp. 327-330.

Dichek, David A. et al., "Seeding of Intravascular Stents With Genetically Engineered Endothelial Cells," *Circulation*, vol. 80, No. 5, Nov. 1989, pp. 1347-1353.

Fischman, David L. et al., "A Randomized Comparison of Cornary-Stent Placement and Balloon Angioplasty in the Treatment of coronary Artery Disease," *The New England Journal of Medicine*, Vo. 331, No. 8, Aug. 25, 1994, pp. 496-501.

Katoh, Osamu et al., "New Double Wire Technique to Stent Ostial Lesions," *Catheterization and Cardiovascular Diagnosis*, vol. 40 (1997) pp. 400-402.

Lewis, Bruce E. et al., "Acute Procedural Reseults in the Treatment of 30 Coronary Artery Bifurcatin Lesions with a Double-Wire Atherectomy Technique for Side-Branch Protection," *American Heart Journal*, vol. 127, No. 6 (1994) pp. 1600-1607.

Nakamura, Shigeru et al., "Techniques for Palmaz-Schatz Stent Deployment in Lesions with a Large Side Branch," *Catheterization and Cardiovascular Diagnosis*, vol. 34 (1995) pp. 353-361.

Satler, Lowell F. et al., "Bifurcation Disease: To Treat or Not to Treat," *Catheterization and Cardiovascular Diagnosis*, vol. 50, (2000) pp. 411-412.

Serruys, Patrick W. et al., "A Comparison of Balloon-Expandable-Stent Implantation with Balloon Angioplasty in Patients with Coronary Artery Disease," *The New England Journal of Medicine*, vol. 331, No. 8, Aug. 25, 1994, pp. 489-495.

Yamashita, Takehiro et al., "Bifurcation Lesions: Two Stents Versus One Stent—Immediate and Follow-up Results," *Journal of the American College of Cardiology*, vol. 35, No. 5, Apr. 2000, pp. 1145-1151.

\* cited by examiner

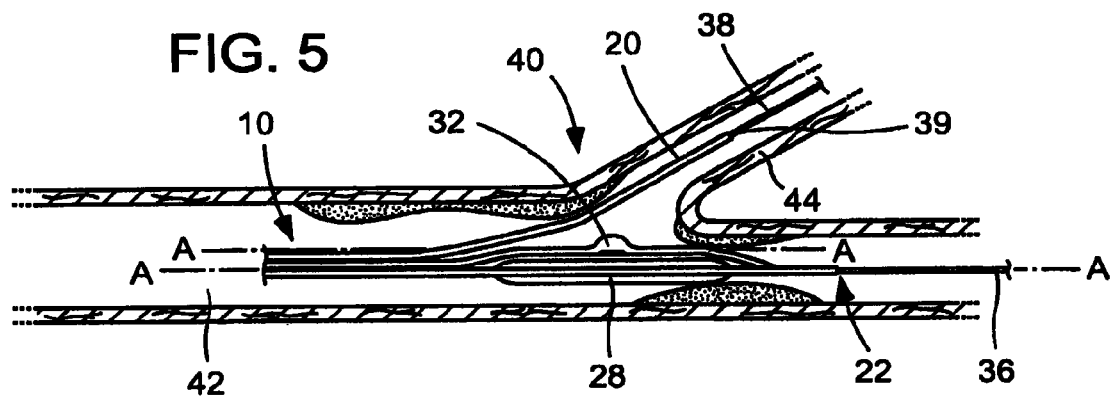
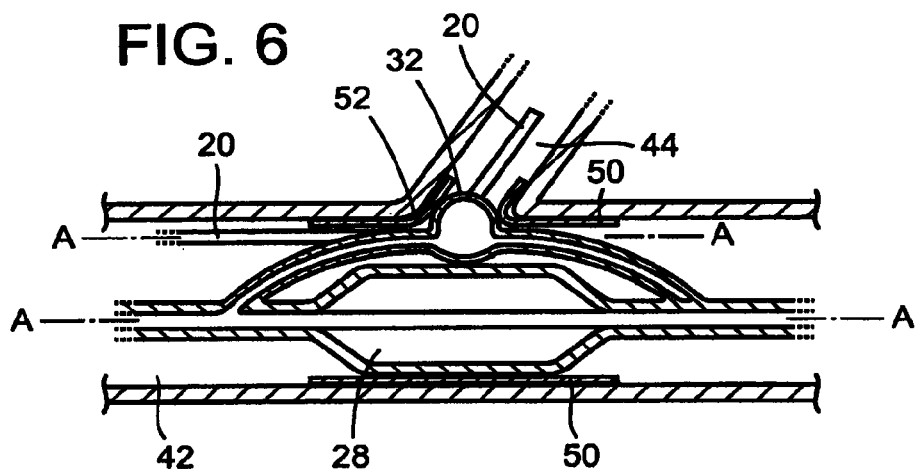
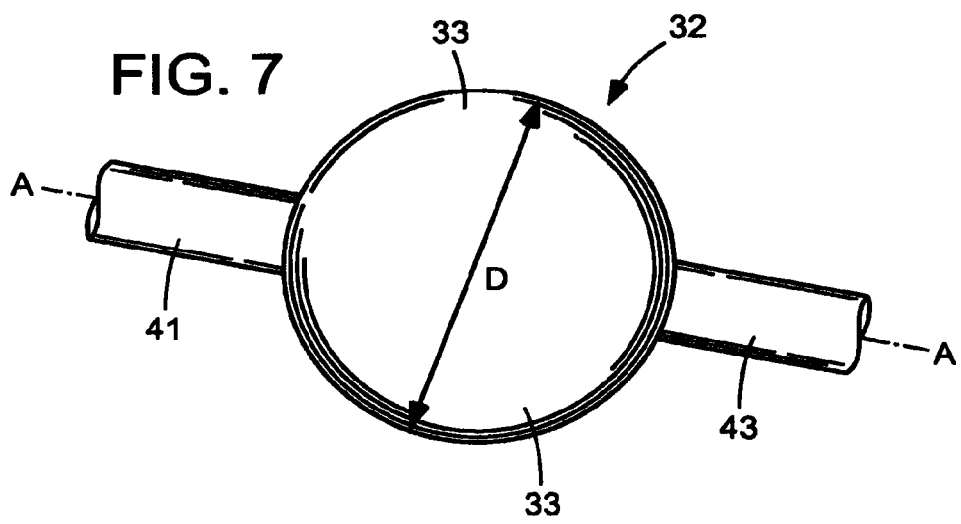

CATHETER BALLOON SYSTEMS AND METHODS

RELATED APPLICATIONS

This application is a continuation of U.S. application Ser. No. 10/834,066, filed on Apr. 29, 2004, entitled "CATHETER BALLOON SYSTEMS AND METHODS", now U.S. Pat. No. 7,655,030, which is a non-provisional of U.S. Provisional Application No. 60/488,006 filed Jul. 18, 2003; and a non-provisional of Provisional Application No. 60/518,870 filed Nov. 12, 2003; and a non-provisional of U.S. Provisional Application No. 60/547,778 filed Feb. 27, 2004; and a non-provisional of U.S. Provisional Application No. 60/548,868 filed Mar. 2, 2004, all of which are hereby incorporated by reference.

FIELD OF THE INVENTION

The present invention relates to the field of medical balloon catheters and, more particularly, to systems for delivering a stent at or near a bifurcation of a body lumen.

BACKGROUND OF THE INVENTION

Balloon catheters, with or without stents, are used to treat strictures, stenoses, or narrowings in various parts of the human body. Devices of numerous designs have been utilized for angioplasty, stents and grafts or combination stent/grafts. Varied catheter designs have been developed for the dilatation of stenoses and to deliver prostheses to treatment sites within the body lumen.

Illustrative procedures involving balloon catheters include percutaneous transluminal angioplasty (PTA) and percutaneous transluminal coronary angioplasty (PTCA), which may be used to reduce arterial build-up such as caused by the accumulation of atherosclerotic plaque. These procedures involve passing a balloon catheter over a guidewire to a stenosis with the aid of a guide catheter. The guidewire extends from a remote incision to the site of the stenosis, and typically across the lesion. The balloon catheter is passed over the guidewire, and ultimately positioned across the lesion.

Once the balloon catheter is positioned appropriately across the lesion, (e.g., under fluoroscopic guidance), the balloon is inflated, which breaks the plaque of the stenosis and causes the arterial cross section to increase. Then the balloon is deflated and withdrawn over the guidewire into the guide catheter, and from the body of the patient.

In many cases, a stent or other prosthesis must be implanted to provide support for the artery. When such a device is to be implanted, a balloon catheter which carries a stent on its balloon is deployed at the site of the stenosis. The balloon and accompanying prosthesis are positioned at the location of the stenosis, and the balloon is inflated to circumferentially expand and thereby implant the prosthesis. Thereafter, the balloon is deflated and the catheter and the guidewire are withdrawn from the patient.

Administering PTCA and/or implanting a stent at a bifurcation in a body lumen poses further challenges for the effective treatment of stenoses in the lumen. For example, dilating a main vessel at a bifurcation may cause narrowing of the adjacent branch vessel. In response to such a challenge, attempts to simultaneously dilate both branches of the bifurcated vessel have been pursued. These attempts include deploying more than one balloon, more than one prosthesis, a bifurcated prosthesis, or some combination of the foregoing.

However, simultaneously deploying multiple and/or bifurcated balloons with or without endoluminal prostheses, hereinafter individually and collectively referred to as a bifurcated assembly, requires accurate placement of the assembly. Deploying multiple stents requires positioning a main body within the main vessel adjacent the bifurcation, and then attempting to position another stent separately into the branch vessel of the body lumen. Alternatives to that include deploying a dedicated bifurcated stent including a tubular body or trunk and two tubular legs extending from the trunk. Examples of bifurcated stents are shown in U.S. Pat. No. 5,723,004 to Dereume et al., U.S. Pat. No. 4,994,071 to MacGregor, and U.S. Pat. No. 5,755,734 to Richter et al.

Additional bifurcation stent delivery systems that provide improved reliable treatment at bifurcations are disclosed, for example, in U.S. Pat. No. 6,325,826 to Vardi et al. and U.S. Pat. No. 6,210,429 to Vardi et al. The contents of these aforementioned patents are incorporated herein by reference.

A need still exists for further improved devices and techniques for treating a bifurcated body lumen. For example, a need further exists for additional stent delivery systems that can be used with stents having a branch access side hole and/or an extendible branch portion.

SUMMARY OF THE INVENTION

The present invention is directed to devices and techniques for treating a bifurcated body lumen including systems for delivering an endoluminal prosthesis at or near a bifurcation of a body lumen. Systems, devices and techniques are disclosed comprising balloon catheters configured to successfully and reliably deploy stents at a bifurcation in a body lumen. Additionally, the balloon catheters can be employed as balloon angioplasty catheters to treat occlusions in blood vessels such as for instance in percutaneous transluminal coronary angioplasty (PTCA) procedures.

According to one aspect, the present invention provides an apparatus for treatment of a bifurcation of a body lumen, the bifurcation comprising a main vessel and a branch vessel, the apparatus comprising: a bifurcated balloon comprising a first branch portion and a second branch portion; the second branch portion comprising an inflatable portion adapted to extend toward the branch vessel, the balloon further comprising a proximal shaft portion and a distal shaft portion connected to the inflatable portion.

According to another aspect, the present invention provides a system for treatment of a bifurcated body lumen, the system comprising: a catheter for insertion into said body lumen, the catheter having a bifurcated distal end comprising first and second branches; and a bifurcated balloon positioned on one of said first and second branches; the balloon having a first balloon branch portion and a second balloon branch portion, the first balloon branch portion including a first inflatable portion and the second balloon branch portion including a second inflatable portion, and wherein the first inflatable portion has a generally cylindrical shape when inflated and the second inflatable portion has a generally offset bulbous shape when inflated.

According to yet another aspect, the present invention provides a method of treating a bifurcation of a body lumen, the bifurcation comprising a main vessel and a branch vessel, the method comprising: (i) introducing a bifurcated balloon and stent assembly into the main branch, the bifurcated balloon comprising at least one inflatable portion; (ii) positioning the assembly at the bifurcation; (iii) inflating the bifurcated balloon thereby expanding the inflatable portion and the stent toward the branch vessel.

According to a further aspect, the present invention provides a balloon catheter, comprising: a catheter having a distal end, a proximal end and an inflation lumen; a balloon formed on the distal end of the catheter, the balloon being in fluid communication with the inflation lumen and being capable of being expanded from an unexpanded configuration to an expanded configuration, wherein the balloon has a herniation in the expanded configuration.

According to still another aspect, the present invention provides a herniated balloon catheter, comprising: a balloon constructed from a composite material and including a woven material formed with a herniation, wherein the balloon has a herniation in the expanded condition.

According to a further aspect, the present invention provides a stent delivery system, comprising: a catheter having a balloon with a herniation; and a stent having an opening including an outwardly expandable portion, the stent being disposed on the balloon with the stent opening aligned with the herniation, whereby upon expansion of the balloon the herniation expands causing the outwardly expandable portion of the stent to extend toward the branch vessel.

According to another aspect, the present invention provides a method for treating a bifurcated vessel, the method comprising: introducing into a vessel a catheter having a distal end, a proximal end, and a guide wire lumen that is adapted to receive a guide wire, a balloon having a distal end and a proximal end, the balloon being disposed near the distal end of the catheter, the balloon having a protrusion at a location between the distal end and proximal end of the balloon, and a stent having a side opening through a wall thereof, the stent being disposed over the balloon, wherein the protrusion of the balloon is positioned through the side opening; positioning the catheter at a bifurcation by aligning the protrusion with a side branch vessel; and expanding the balloon so as to expand the stent such that the side opening is aligned with the opening of the bifurcated vessel.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention.

FIG. 5 is a view of the stent delivery system of FIG. 1 in a blood vessel located at a bifurcation in the vessel without a stent mounted thereon in accordance with a method of the present invention.

FIG. 6 is a cross-sectional side view of the stent delivery system of FIG. 1 with a stent mounted thereon and shown in the expanded condition.

FIG. 7 is a perspective view of a balloon configured according to one embodiment of the present invention.

DESCRIPTION OF THE PREFERRED EMBODIMENTS

The present invention relates to balloon catheters such as balloon angioplasty catheters to treat occlusions in blood vessels. The balloon catheters can be used alone or with a stent, prosthesis or graft. Such a stent delivery system can be used for placement of a stent in a body lumen, particularly at vessel bifurcations. A preferred stent to be delivered is generally configured to at least partially cover a portion of a branch vessel as well as a main vessel. In general, a wide variety of stents and deployment methods may be used with the stent delivery system embodiments of the present invention and the present invention should be understood to not be limited to any particular stent design or configuration. Examples of the types of stents that may be used with the delivery systems of the present invention are disclosed, for example, in U.S. Pat. No. 6,210,429 to Vardi et al., U.S. Pat. No. 6,325,826 to Vardi et al., and co-pending U.S. patent application Ser. No. 10/644,550, entitled "Stent With a Protruding Branch Portion For Bifurcated Vessels," the entire contents of which are incorporated herein by reference. In general, the aforementioned stent includes a branch portion located at some point along the length of the stent that is configured to be extendible into a branch vessel in a vessel bifurcation. Once the stent is in position in the main vessel and the branch portion is aligned with the side branch vessel the stent can be expanded and the delivery system is particularly adapted to expand the stent branch portion into the side branch vessel. The stent, including the branch portion, may be expanded with a single expansion or multiple expansions.

Figure 1:
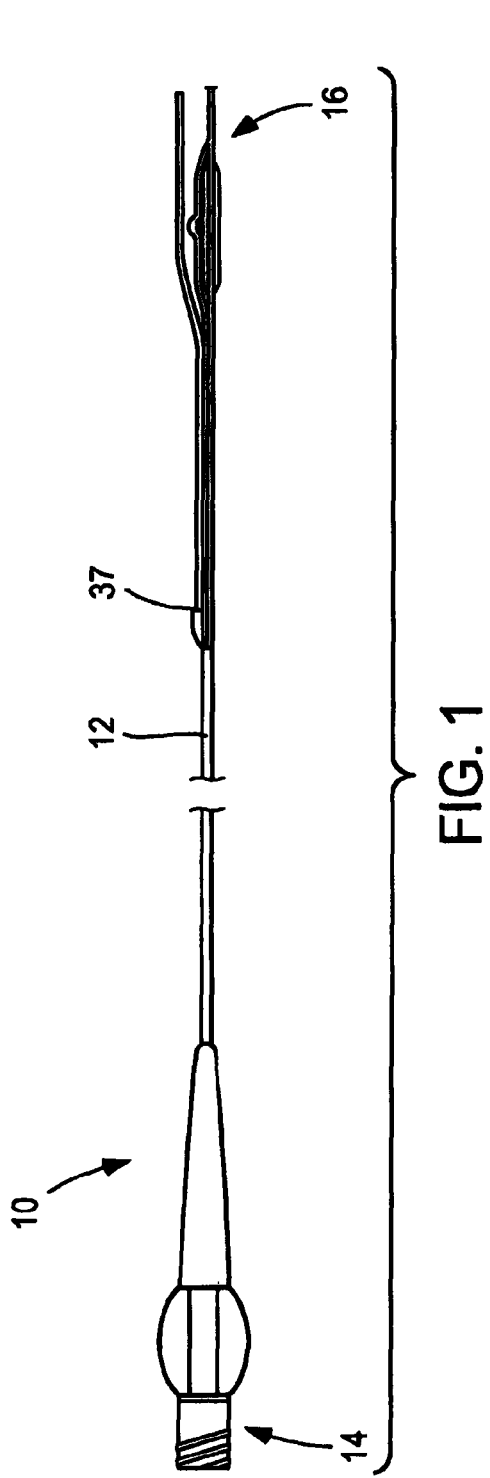
FIG. 1 is a side view of an illustrative embodiment of a stent delivery system constructed in accordance with the present invention.
Figure 2:
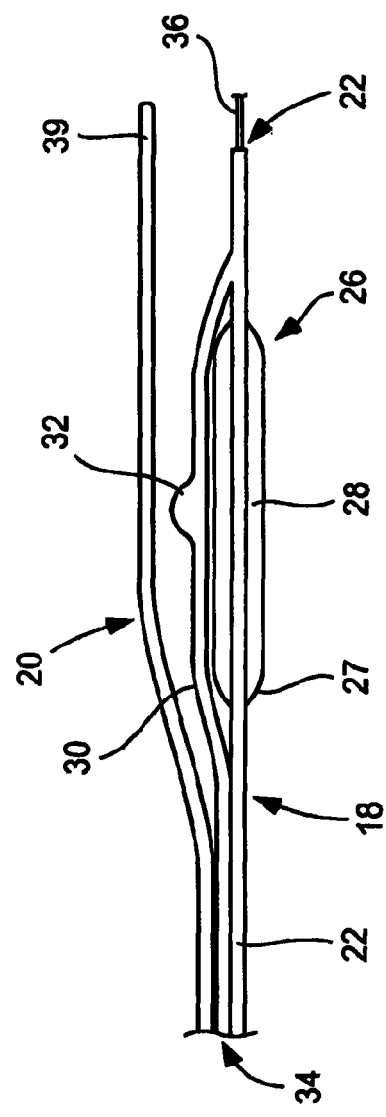
FIG. 2 is an enlarged side view taken of the distal portion of the system of FIG. 1.

An illustrative view of one embodiment of a stent delivery system 10 constructed in accordance with the present invention is shown in FIG. 1. Stent delivery system 10 generally comprises an elongate main catheter shaft 12 extending from a proximal end 14 to a distal end 16. As best seen in FIG. 2, distal end 16 has a bifurcated tip structure with two branch portions, a main vessel branch portion 18 and a side branch sheath 20 that branch off of main catheter shaft 12. A bifurcated balloon 26 is attached to main vessel branch portion 18 adjacent the distal end 16 and comprises first and second branch portions 27, 30. First branch portion 27 of balloon 26 comprises an elongate inflatable portion 28. Second branch portion 30 of balloon 26 comprises a second inflatable portion or auxiliary inflatable portion 32. Second branch portion 30 includes an inflation lumen that branches off from first branch portion 27 proximally from the balloon 26 and extends substantially adjacent elongate inflatable portion 28. The distal end of second branch portion 30 is attached to first branch portion 27 at a location distally from the balloon 26. In one preferred embodiment, the distal end of branch portion 30 is fixedly attached distally of balloon 26 in order to prevent at least the second inflatable portion 32 from moving around the first branch portion 27, although in alternate embodiments it may be removably attached.

In a preferred embodiment, first inflatable portion 28 is generally cylindrical and extends coaxially along main vessel branch portion 18. Second inflatable portion 32 may have a shape and size adapted to extend into the branch vessel as shown and described herein. For example, portion 32 may have a generally offset configuration and may be positioned adjacent or in abutting relation with respect to elongate inflatable portion 28.

The first and second inflatable portions can have varied shapes, sizes and positioning in accordance with the principles of the invention. For example, in alternative design variations, accurate sizing and positioning of the inflatable portions relative to the vessel may be achieved.

According to the present invention, the inflatable portions, or balloons, can be constructed of any suitable material. For example, the balloons may be constructed of an appropriate polymeric material. Particular examples include the polyamide family, or the polyamide blend family, polyethylene (PE), polyethylene terephthalate (PET), polyurethanes, polyamides, and polyamide blends such as PBAX. The compliance of the first inflatable portion 28 and the second inflatable portion 32 can be the same or different. In one preferred embodiment, second inflatable portion 32 is longitudinally positioned at a generally central location relative to the first inflatable portion 28. In alternate embodiments, second inflatable portion 32 may be positioned at any position adjacent first inflatable portion 28.

In a preferred embodiment, balloon branch portions 27 and 30 have a common inflation lumen 34. Inflation lumen 34 can be conventional, and extend from a portion of the stent delivery system which always remains outside of the patient (not pictured). Inflation lumen 34 extends distally into each of first and second branch portions 27 and 30 and thus, inflation lumen 34 is in fluid communication with the interiors of first inflatable portion 28 and second inflatable portion 32. Thus inflation lumen 34 is used to supply pressurized inflation fluid to first inflatable portion 28 and second inflatable portion 32 when it is desired to inflate balloon 26. Inflation lumen 34 is also used to drain inflation fluid from first inflatable portion 28 and second inflatable portion 32 when it is desired to deflate the balloon. First and second inflatable portions are initially deflated when directing the stent delivery device to the bifurcation lesion in a patient. In this embodiment, the inflation lumen 34 inflates inflatable portions 28, 32 substantially simultaneously. In an alternative embodiment, branch balloon portions 27 and 30 have separate inflation lumens. In this alternative embodiment inflatable portions 28 and 32 can be inflated simultaneously or sequentially. When sequential inflation is desired, preferably, the first inflatable portion 28 is inflated first, followed by the inflation of the second portion 32.

First main guidewire lumen 22 extends through main vessel branch portion 18 and first inflatable portion 28. Although first guidewire lumen 22 extends through first inflatable portion 28 in the embodiment depicted in FIGS. 1-2, it is distinct from inflation lumen 34 and is not in fluid communication with the interior of balloon 26 as shown. Preferably, the first guidewire lumen 22 extends distally of first inflatable portion 28 and has an open distal end. Alternatively, guidewire lumen 22 can extend through branch portion 30.

In the embodiment depicted in FIGS. 1-2, an optional side sheath 20 is illustrated which does not include an inflatable balloon. Although in alternate embodiments side sheath 20 could include an inflatable portion, as described for example in co-pending U.S. patent application Ser. No. 10/644,550 entitled "Stent With a Protruding Branch Portion For Bifurcated Vessels". Side sheath 20 is exterior to and distinct from inflation lumen 34 and thus is also not in fluid communication with the interior of balloon 26 as shown. As shown in the embodiment of FIGS. 1-2, side sheath 20 preferably extends distally of balloon 26, and may include a proximal open end 37 at any point along the length of the stent delivery system and a distal open end 39. Side sheath 20 can be of the type as described in U.S. Pat. No. 6,325,826 to Vardi, et al., for example, and in operation the side sheath 20 can extend through a branch access hole of the stent.

Figure 3:
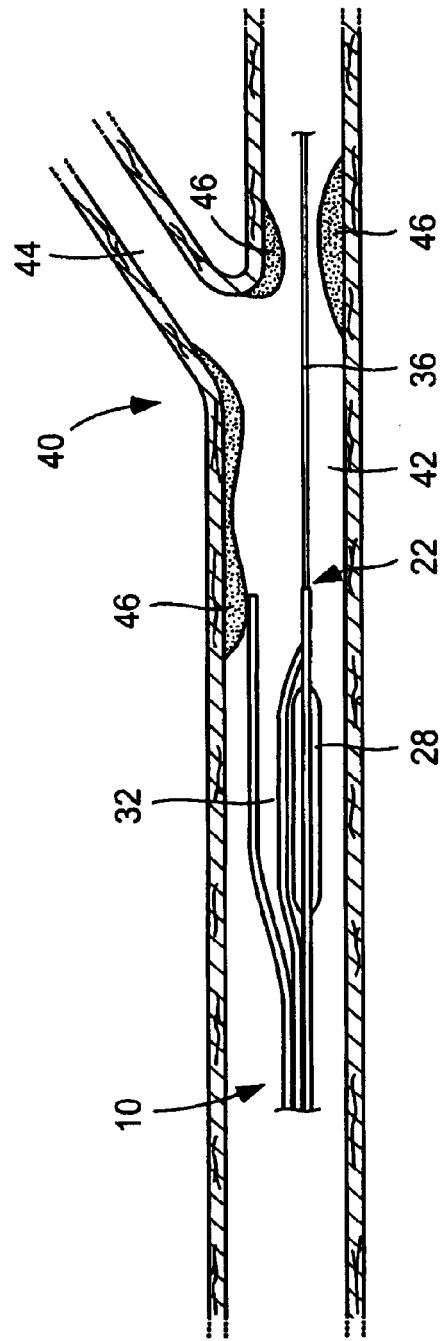
FIG. 3 is a view of the stent delivery system of FIG. 1 in a blood vessel shown approaching a bifurcation in the vessel without a stent mounted thereon in accordance with a method of the present invention.
Figure 4:
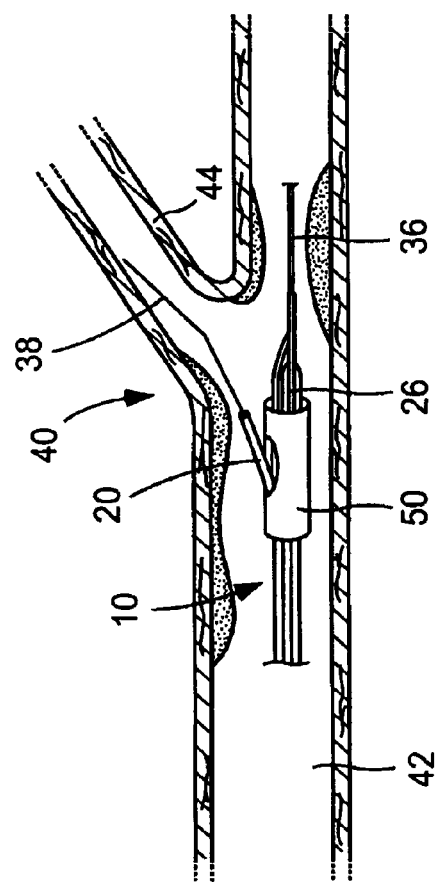
FIG. 4 is a view of the system of FIG. 3, including a stent mounted thereon.

With reference to FIGS. 3-6, an exemplary manner of practicing the invention will now be discussed. Referring to FIGS. 3 and 5, the delivery system is shown in relation to an exemplary body lumen adjacent a blood vessel bifurcation 40 usually comprised of plaque and the delivery system 10 is shown without a stent mounted thereon (FIGS. 3 and 5). FIGS. 4 and 6 show the stent delivery system 10 with a stent 50 mounted thereon.

Bifurcation 40 includes a main vessel 42 and a branch vessel 44. Illustrative obstructions 46 located within bifurcation 40 may span or at least partially obstruct main vessel 42 and a proximal portion branch vessel 44. Generally, stent delivery system 10 may be threaded over a first main guidewire placed in the main vessel to guide the delivery system to the treatment site. More specifically, the proximal end of first guidewire 36 is threaded into the distal open end of the main guidewire lumen 22 and the delivery system is tracked to a position at or near bifurcation 40, as depicted in FIG. 3. Second guidewire 38 (FIG. 5) is then threaded into stent delivery system 10 from the proximal end of the delivery system. More specifically, second guidewire 38 is threaded into the open proximal end 37 of side sheath 20, and may extend therefrom through the open distal end 39 of side sheath 20, as depicted in FIG. 5. Alternatively, second guidewire 38 can be resting dormant on the inside of the side sheath, and when the system is proximal the bifurcation 40, it can be advanced out of side sheath 20 into side branch vessel 44. The systems in accordance with the principles of the invention may be used in over-the-wire or rapid exchange systems, which may include rapid exchange on either or both of the side sheath or main catheter. Rapid exchange is described in one exemplary embodiment in US2003/0181923 to Vardi et al., published Sep. 25, 2003, the entire contents of which are incorporated herein by reference.

In one embodiment, the stent delivery system 10 is positioned near bifurcation 40, and with the distal end 16 (FIG. 1) positioned near side branch vessel 44 (FIGS. 3-6), second guidewire 38 is advanced into side branch vessel 44 from side sheath 20. Then, the first and second inflatable portions of balloon 26 are positioned adjacent the opening of side branch vessel 44 such that auxiliary inflatable side portion 32 of bifurcated balloon 26 is aligned with side branch vessel. In one exemplary embodiment, alignment may be achieved using markers, as described in U.S. Pat. No. 6,692,483 to Vardi, et al., the entire contents of which is incorporated herein by reference. Second guidewire 38 remains in side branch sheath 20, and the distal end 16 of system 10 remains in main vessel 42. First guidewire 36 remains within first guidewire lumen 22, and may be further advanced and positioned in main branch vessel 42.

Once the system is properly positioned, pressurized fluid is supplied to first and second inflatable portions 28 and 32, respectively, of balloon 26 to dilate the body lumen and expand a stent mounted thereon (FIG. 6). Preferably, the inflatable portion 28 expands the main body of the stent and inflatable portion 32 expands the side (opening) and expandable branch structure of the stent, as discussed in more detail with reference to FIG. 6. After inflatable portions 28 and 32 have been inflated as described above, balloon 26 is deflated by draining the inflation fluid via inflation lumen 34. This allows the inflatable portions 28 and 32 to collapse in preparation for withdrawal of the assembly from vessel 42.

Referring now to FIGS. 4 and 6, one preferred embodiment is shown with stent delivery system 10 and an exemplary stent 50 mounted on the exterior of distal end 16 of the stent delivery system. Stent 50 includes an extendible branch portion 52 configured to extend into a branch vessel as discussed in co-pending U.S. application Ser. No. 10/644,550, entitled "Stent with Protruding Branch Portion for Bifurcated Vessels". The second inflatable portion 32 may be configured and positioned to deploy the outwardly expanding stent elements or branch portion 52 and may be positioned adjacent to the branch portion 52, or into a side branch access opening in the stent. As shown in FIG. 6, when first and second inflatable portions 28 and 32 are expanded, they simultaneously or sequentially, depending upon the configuration of the inflation lumen, cause the stent 50 to expand in the main vessel 42 and the branch portion 52 of stent 50 to be pushed or extended into the branch vessel 44. Upon inflation of the balloon 26, the second inflatable portion 32 expands and extends the branch portion 52 toward the branch vessel to open and support the entrance or ostium of the side branch artery. This would occur simultaneously when the balloons share a common inflation lumen but could be sequentially if separate inflation lumens are used. Although a bifurcated balloon is depicted, as shown, more than two inflatable portions or more than two balloons may be utilized with the present invention.

As illustrated, for example, in FIGS. 5 and 6, the first and second branch portions 27 and 30 have a longitudinal axis A. The longitudinal axes are substantially parallel with each other. The term "substantially parallel" is intended to encompass deviations from a purely parallel relationship which may be caused by flexure of the branch portions 27 and 30, or other components, experienced during insertion, travel, and deployment within a body lumen.

FIG. 7 is an enlarged perspective view of the auxiliary inflatable side portion 32 of bifurcated balloon 26, which is referred to in the previous embodiments depicted in FIGS. 1-6. According to this embodiment, the central portion 33 of the auxiliary inflatable side portion 32 extends in a generally equidistant manner from the longitudinal axis A, and at an angle of up to about 90° relative to longitudinal axis A, but other angles are contemplated. As illustrated in FIG. 7, the auxiliary inflatable side portion 32 can have a generically spherical central portion 33 which is connected to a proximal shaft 41, as well a distal shaft 43. The components of the auxiliary inflatable side portion 32 may be sized appropriately, as will be readily apparent to those skilled in the art. The central spherical portion 33 can be provided with a suitable inflated diameter D. The diameter D can vary according to various factors known to those skilled in the art. According to a non-limiting, exemplary embodiment, the diameter D can be on the order of a few millimeters. For example, the diameter D is on the order of about 1.5-6.0 mm and, preferably, on the order of about 3.34-3.36 mm.

Figure 8:
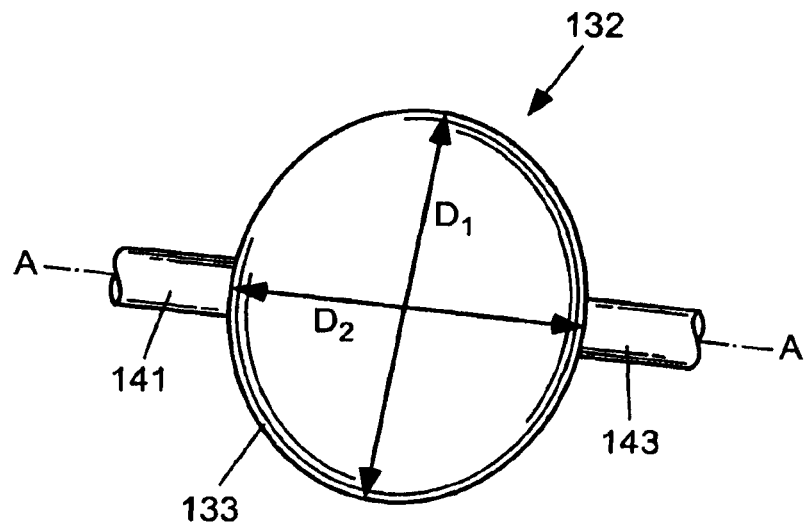
FIG. 8 is a perspective view of a balloon constructed according to an alternative embodiment of the present invention.

FIG. 8 illustrates an alternative auxiliary inflatable side portion construction 132. According to this embodiment, the central portion 133 of the auxiliary inflatable side portion 132 extends in a generally equidistant manner from the longitudinal axis A, and at an angle of up to about 90° relative to longitudinal axis A, but other angles are contemplated. As illustrated in FIG. 8, the balloon 132 comprises a generally elliptical central portion 133, as well as a proximal shaft portion 141, and distal shaft 143 connected thereto. As with the previous embodiment, the various components of the balloon 132 may be sized as appropriate within appropriate dimensional ranges, as determined by those skilled in the art. The elliptical central section 133 of the balloon 132 is provided with major and minor diameters, D1 and D2, respectively, as illustrated in FIG. 7. According to non-limiting exemplary embodiments, the elliptical central section may be shaped such that the ratio D2/D1 is on the order of about 0.8. According to further exemplary non-limiting embodiments, the major diameter D1 is preferably on the order of about 3.65-3.85 mm and can range from 1.5-6 mm, while the minor diameter D2 is smaller than D1 and is preferably on the order of about 2.9-3.1 mm.

Figure 9:
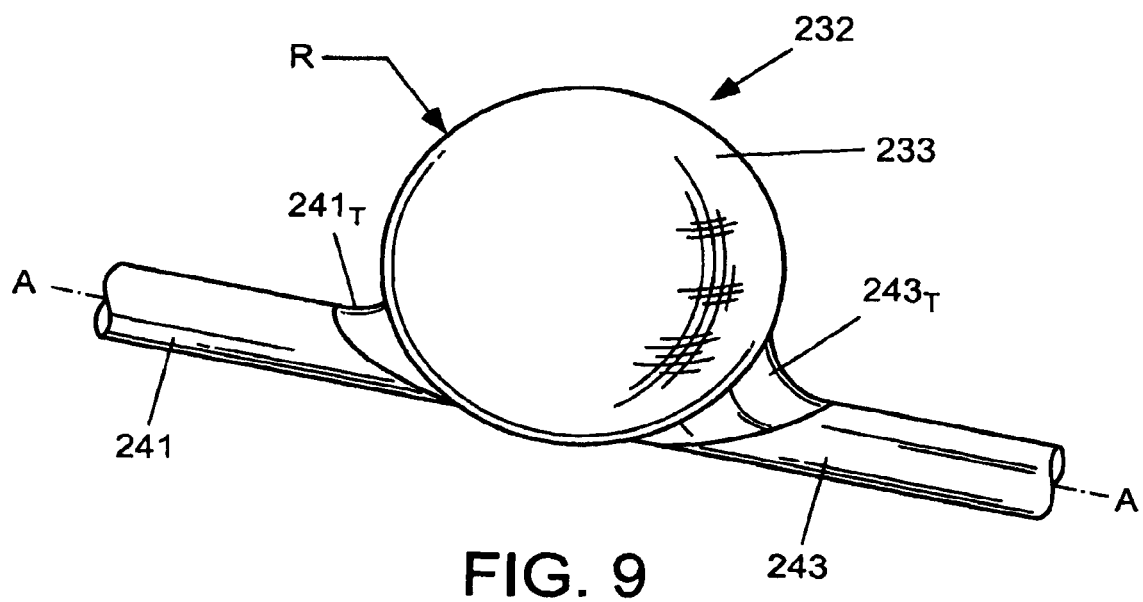
FIG. 9 is a perspective view of a balloon configured according to a further embodiment of the present invention.

FIG. 9 illustrates yet a further embodiment of auxiliary inflatable side portion 232 of bifurcated balloon 26 constructed according to the principles of the present invention. According to this embodiment, the central portion 232 is offset relative to the longitudinal axis A and preferably extends toward and/or into the branch vessel 44. The central portion 232 may extend at an angle of up to about 90° relative to longitudinal axis A, but other angles are contemplated. As illustrated in FIG. 9, the auxiliary inflatable side portion 232 of balloon 26 comprises an offset central bulbous or generally spherical portion 233, with a proximal shaft portion 241 and distal shaft portion 243 connected thereto via a proximal transition section $241_T$ and distal transition $243_T$, respectively. As with the previous embodiments, the various components of the auxiliary inflatable side portion 232 of balloon 26 can be sized as appropriate, and as readily determined by those skilled in the art. According to exemplary, non-limiting embodiments, the auxiliary inflatable side portion 232 of balloon 26 can be configured such that the central offset portion 233 is provided with a radius of curvature R which is on the order of about 0.50-3.0 mm.

Figure 10:
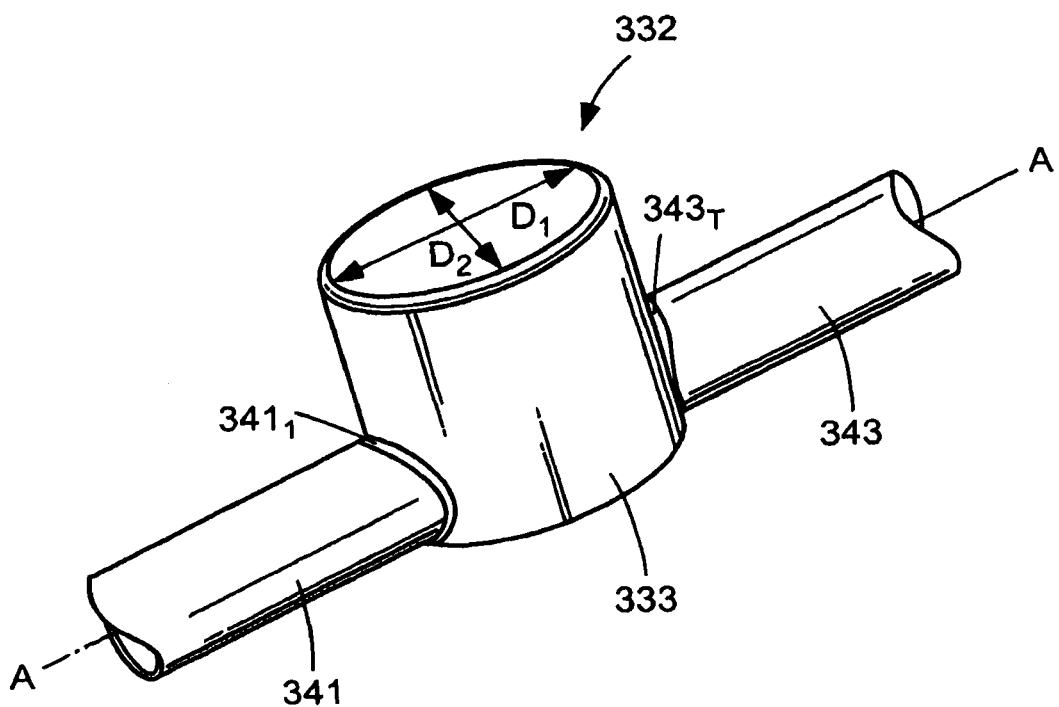
FIG. 10 is a perspective view of a balloon configured according to yet another alternative embodiment of the present invention.

FIG. 10 illustrates yet another alternative embodiment for an auxiliary inflatable side portion 332 of bifurcated balloon member 26. According to this embodiment, the central portion 332 is offset relative to the longitudinal axis A and preferably extends toward and/or into the branch vessel 44 (not shown). The central portion 332 may extend at an angle of up to about 90° relative to longitudinal axis A, but other angles are contemplated. As shown in FIG. 10, the auxiliary inflatable side portion 332 is configured such that it comprises a generally offset elliptical and cylindrical central section 333, with proximal shaft portions 341 and distal shaft portions 343 connected thereto via proximal transition section $341_1$ and distal transition portion $343_T$, respectively. The offset central section 333 is preferably configured such that it comprised a first diameter D1 and second diameter D2 wherein D1 and D2 have different values (D1≠D2). The dimensions of the various constituent components of the auxiliary inflatable side portion 332 can be determined by those skilled in the art. According to exemplary non-limiting embodiments, the auxiliary inflatable side portion 332 can be configured such that it is provided with first and second diameters such that the ratio D2/D1 is on the order of about 0.25-4.0 mm. According to further, non-limiting examples, the auxiliary inflatable side portion 332 can be configured such that it is provided with a first diameter D1 which has dimensions on the order of about 1.5-6.0 mm and, preferably about 2.7-2.9 mm, and a second diameter D2 which has dimensions on the order of about 1.5-6.0 mm, and preferably about 2.1-2.3 mm.

Figure 11:
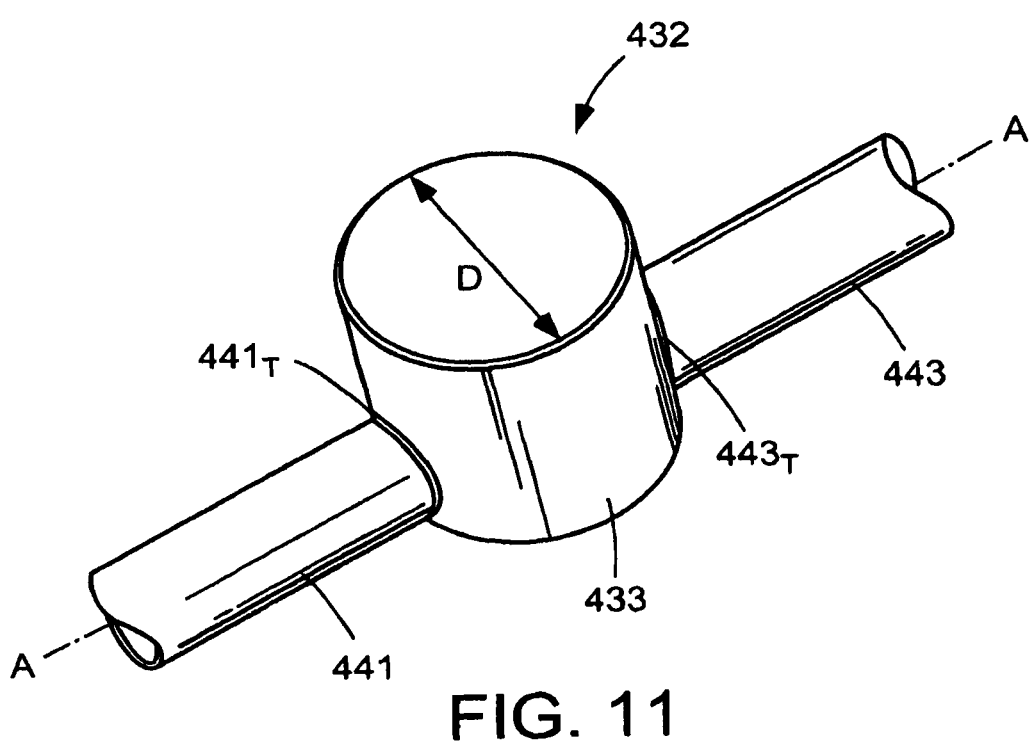
FIG. 11 is a perspective view of a balloon configured according to another embodiment of the present invention.

FIG. 11 illustrates yet another alternative embodiment of an auxiliary inflatable side portion 432 of bifurcated balloon 26. According to this embodiment, the central portion 432 is offset relative to the longitudinal axis A and preferably extends toward and/or into the branch vessel 44 (not shown). The central portion 432 may extend at an angle of up to about 90° relative to longitudinal axis A, but other angles are contemplated. The auxiliary inflatable side portion 432 is configured such that it comprises an offset generally cylindrical central section 433 having a proximal shaft portion 441 and a distal shaft portion 443 connected thereto via proximal transition shaft portion $441_T$ and distal transition portion $443_T$, respectively. The various constituent components of the balloon 432 can be configured with relative dimensions which can be ascertained by those skilled in the art. According to exemplary, non-limiting examples, the balloon 432 can be configured such that it is provided with an offset generally cylindrical central section 433 having a diameter D which is on the order of about 1.5-6.0 mm.

FIGS. 12-15 illustrate further alternative embodiments of the present invention which can be utilized in the treatment of branch arteries, including incorporation into stent-delivery systems of the type previously described. The balloons depicted in the embodiments of FIGS. 12-15 can be referred to as "herniated" balloon configurations that function in a manner similar to the embodiments described above. The herniated balloon configuration is characterized by having a generally cylindrical shape in an unexpanded configuration, and a generally cylindrical shape with a generally hemispherical appendage that inflates outwardly relative to the longitudinal axis of the balloon toward the branch artery in an expanded state or configuration. This protrusion can be referred to as a herniation, bulge, protrusion, or extension. The particular shape, size, and configuration of the balloon and the herniations illustrated herein are exemplary, and may be modified from that explicitly shown and described. The expandable herniation, bulge, protrusion, or extension can be expandable towards the entrance of side branch (e.g.—44, FIG. 3) over a suitable dimension, such as 1-4 mm.

The embodiments of the balloons depicted in FIGS. 12-15 can be utilized in a manner similar to that which has been described in connection with previously illustrated embodiments (see, e.g.—FIGS. 1-6).

Figure 12:
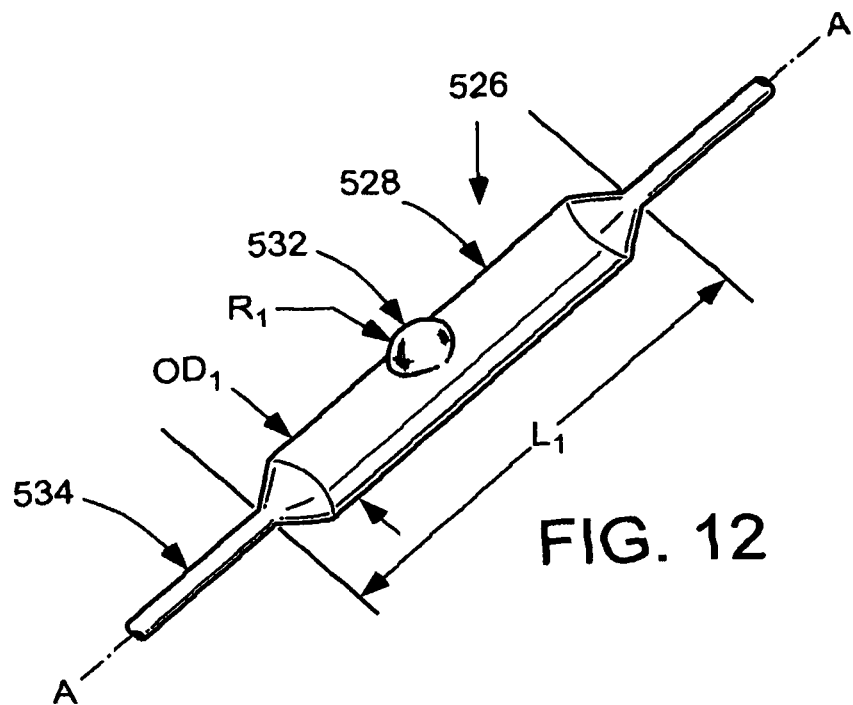
FIG. 12 is a perspective view of a balloon catheter configured according to another embodiment of the present invention.

With regard to the embodiments depicted in FIGS. 12-15, it should be understood that the herniated balloon constructions depicted therein can be utilized as one or more of the first and second inflatable portions of a bifurcated balloon (e.g. 26, FIGS. 1-6). Alternatively, the herniated balloon constructions can be utilized in place of a bifurcated-type balloon. In other words, the herniated balloon can be utilized by itself instead of a balloon construction which relies upon distinct first and second inflatable portions. An exemplary embodiment of a herniated balloon catheter 526 is illustrated in FIG. 12. In the illustrated embodiment, the herniated balloon catheter 526 comprises an elongated inflatable portion 528 and a herniation, bulge, protrusion, or extension 532 therewith. In the embodiment of FIG. 12 the balloon catheter further includes a lumen 534 which can serve to communicate pressure for inflation of the balloon catheter 526, and provide a passage way for a guide wire, etc.

The particular configuration and dimensions of the balloon catheter 526 can vary according to a number of factors. For purposes of illustration only, certain suitable, but non-limiting, dimensions of various components of the balloon catheter 526 will now be described. The balloon catheter 526 can be provided with a length dimension $L_1$ which is about 4-100 mm. The balloon can be provided with an outside diameter $OD_1$ which is on the order of about 1-10 mm, and the herniation 532 can be provided with a radius of curvature $R_1$ which is about 0.5-3 mm.

Figure 13:
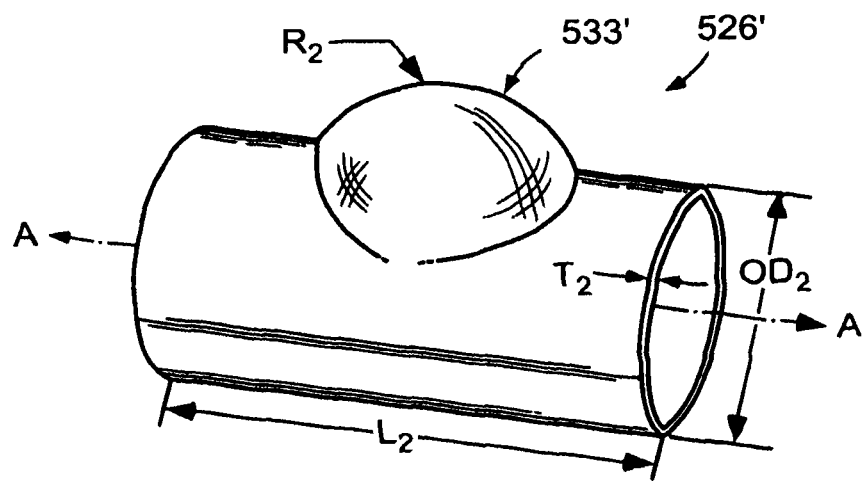
FIG. 13 is a perspective view of a portion of a balloon constructed according to the principles of the embodiment of FIG. 11.

FIG. 13 illustrates a portion 526' of a herniated balloon catheter, which includes a herniation 533'. According to further non-limiting examples, the balloon portion 526' can be provided with the following suitable dimensions: outside diameter $OD_2$ of 1-10 mm; a length dimension $L_2$ of about 4-100 mm; a wall thickness dimension $T_2$ of about 0.003-0.005 mm and a radius of curvature $R_2$ of the herniated portion 533' of about 0.05-3 mm.

Figure 14:
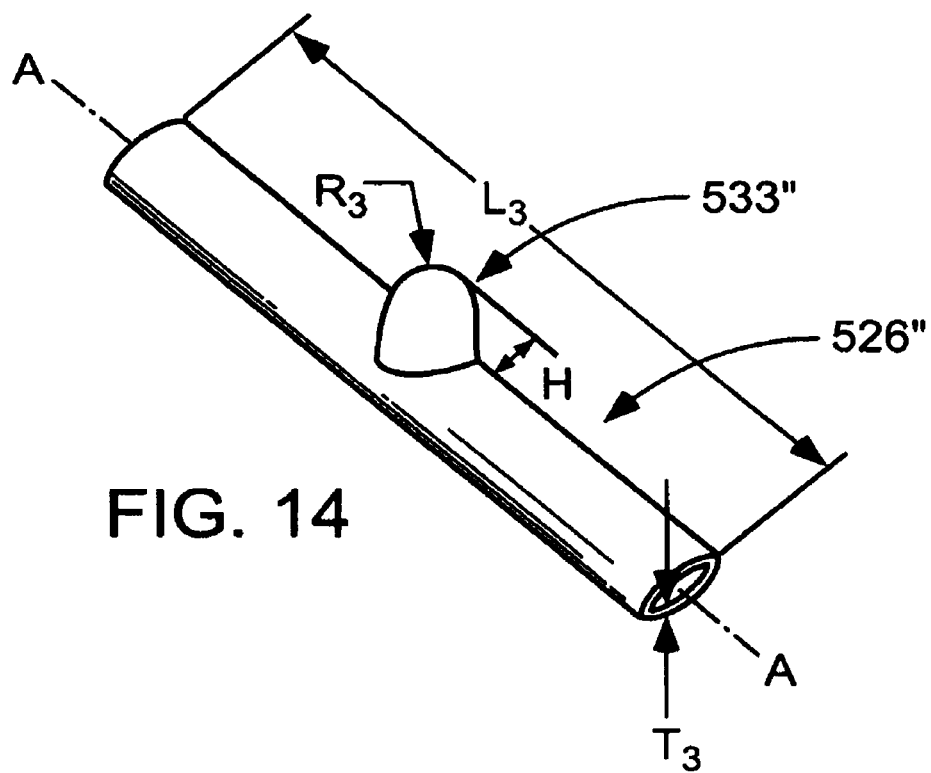
FIG. 14 is a perspective view of a portion of a balloon constructed according to an alternative embodiment of the present invention.
Figure 15:
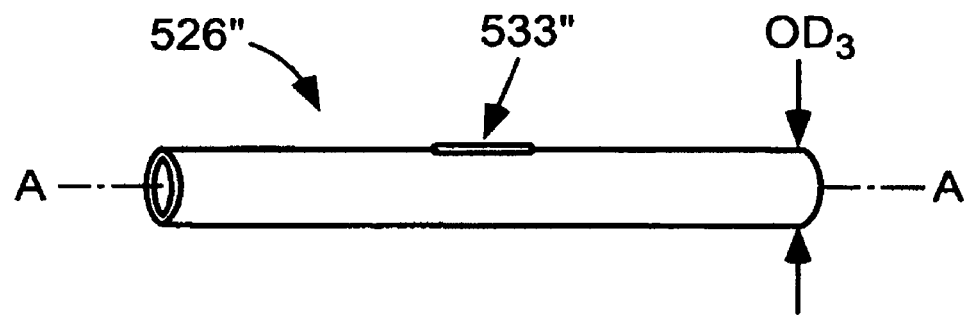
FIG. 15 is a side view of the balloon of FIG. 13 shown in an unexpanded state.

Another alternative herniated balloon construction is shown in FIG. 14, where the herniated balloon portion 526" is provided with an alternatively configured herniation 533". Illustrative and non-limiting examples of suitable dimensions according to this embodiment include: an outside diameter $OD_3$ (FIG. 15) of about 1-10 mm; a length dimension $L_3$ of about 4-100 mm; a height dimensions H of the herniation 533" of about 1-6 mm; and a radius of curvature $R_3$ of the herniation 533" of about 0.5-3 mm; and a wall thickness of the herniated balloon catheter portion 526" of about 0.01 mm.

Although the herniation 533, 533', and 533" of the embodiments illustrated in FIGS. 12-15 are shown as being centrally located on the herniated balloon catheter 526 or herniated balloon catheter portions 526', 526", it should be noted that the herniation 533, 533', and/or 533" maybe located at any desired position along the length of the balloon. For example, once associated with a stent, it can preferably be placed such that it corresponds to the location along the middle ⅓ of the stent.

The balloon 526, 526', and/or 526" can be constructed of any suitable material such as those previously disclosed herein. In addition, the balloon 526, 526', and/or 526" can be constructed of a composite material. Suitable materials include a combination of elastomeric and semi to non-compliant materials such as: urethane; silicone; nylon; latex; (elastomeric) polyethylene hytrel pebax polyaryletherthketone; polyoxymethylene; polyamide; polyester thermoplastic polyetheretherkatone; and polypropylene (semi non-compliant). The balloon 526, 526', and/or 526" can be also be constructed by combining the above-disclosed materials with woven textile materials such as Kevlar, silk, cotton, wool, etc. This can be accomplished by winding or weaving a textile material onto a rod that has the shape of the desired herniated balloon. The polymer component of the composite is then extruded or dip-coated over the rod. This composite structure is then cured, heat set, or adhesively fused together. The rod is then removed and the remaining shape comprises the herniated balloon 526, 526', and/or 526".

The herniation 533, 533', and/or 533" can be provided by adding an appendage to a conventional balloon by using a molded collar or adhesively attaching an object to the surface of the balloon, or by using a mound of adhesive to create the herniation.

The balloon 526, 526', and/or 526" can be constructed by molding three small balloons and attaching them in tandem. The central balloon comprises the desired shape of the herniation. These balloons would share a common inflation port. When the balloons are inflated, the center balloon expands in the desired manner to form the herniation.

Figure 16:
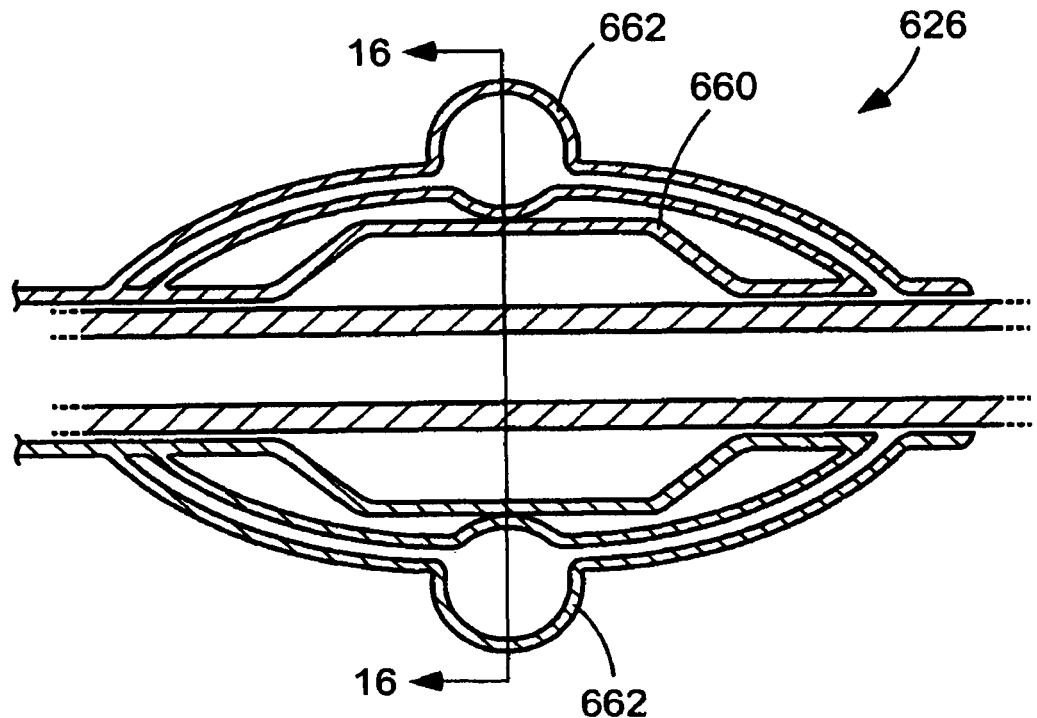
FIG. 16 is a cross-sectional view of an alternative embodiment of a balloon in an expanded state constructed according the principles of the present invention.
Figure 17:
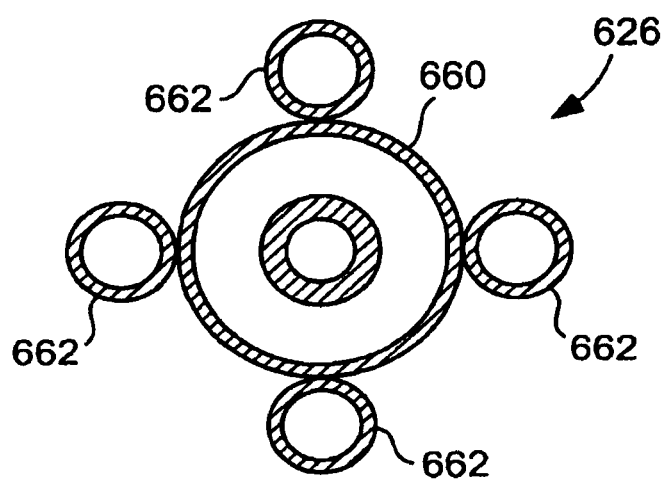
FIG. 17 is a cross-sectional view of an alternative embodiment of a balloon constructed in accordance with the present invention.
Figure 18:
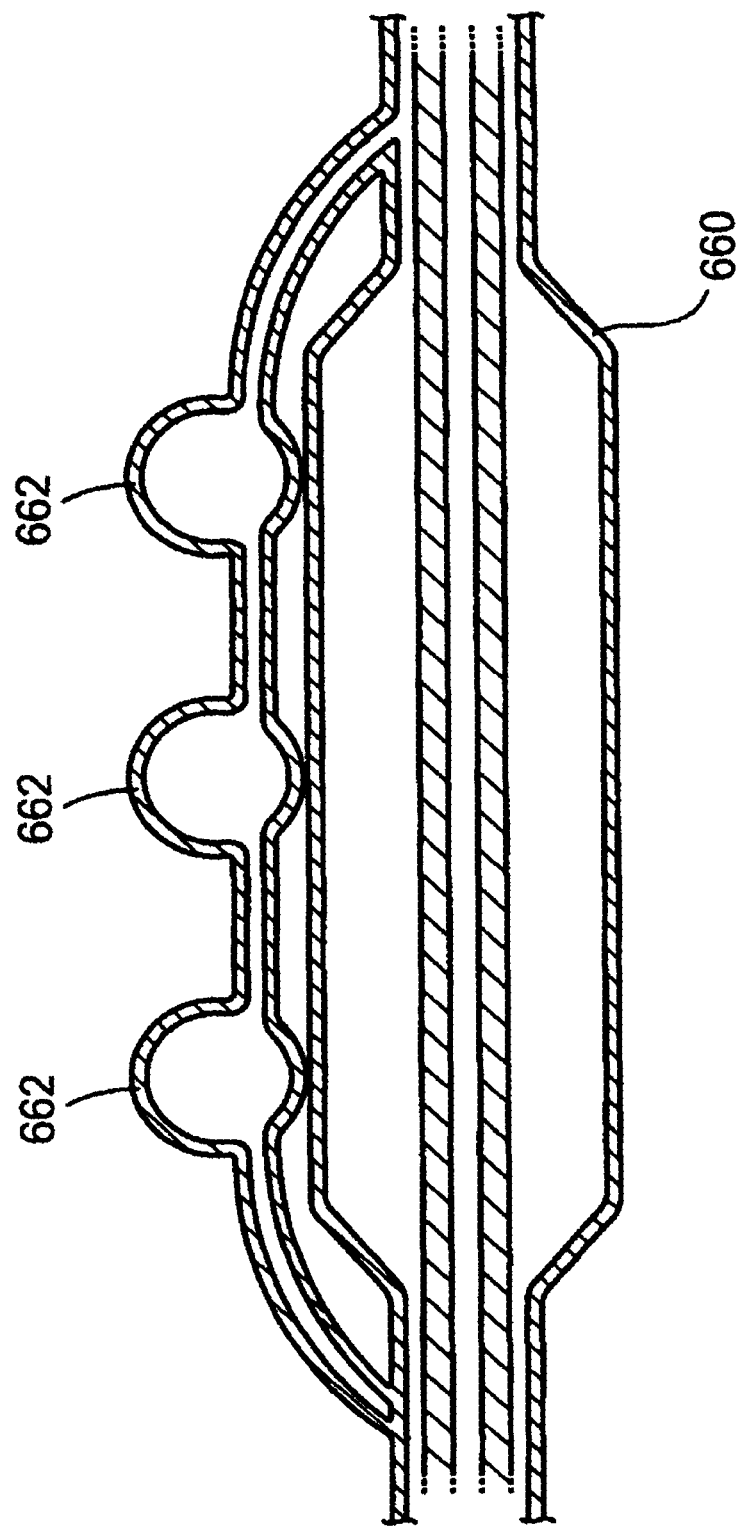
FIG. 18 is a cross-sectional view of yet another alternative embodiment of a balloon constructed in accordance with the present invention.

According to further aspects of the present invention, more than two inflatable portions or more than two balloons may be utilized. For example, as shown in FIGS. 16-18, the balloon may include a plurality of second inflatable portions. In this regard, a user may be able to treat multiple bifurcations with a single device. Such a configuration may also eliminate the need for a secondary positioning lumen (side sheath 20) and reduce the profile of the system. As shown in FIGS. 16-17, in one exemplary embodiment, balloon 626 includes four inflatable portions 662 positioned radially around a first inflatable portion 660. In an alternate embodiment, shown in FIG. 18, a plurality of inflatable balloon portions 662 are spaced longitudinally adjacent one side of first inflatable portion 660.

Figure 19:
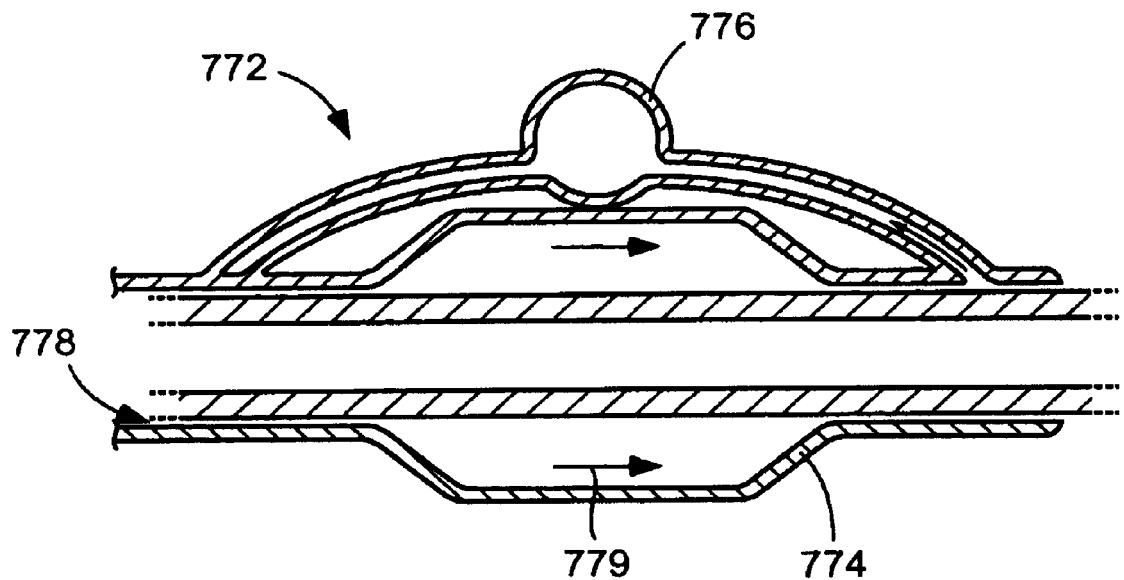
FIG. 19 is a cross-sectional view of yet another alternative embodiment of a balloon constructed in accordance with the present invention.

Referring to FIG. 19, a cross-sectional view of an alternative embodiment of a balloon 772 is shown. Balloon 772 includes a main inflatable portion 774 and further extends into secondary inflatable portion 776. Lumen 778 can be of various diameters, compliances, and materials to control the timing and size of the secondary expandable portion 776 upon inflation. In one embodiment, second expandable portion 776 may deploy subsequent to main expandable portion 774. Such a time delay may be achieved, for example, using a smaller diameter inflation lumen leading up to secondary expandable portion 776 since the inflation fluid travels along path 779 first through the main expandable portion 774 and then on to secondary expandable portion 776. In this regard, delivery system 770 may permit sequential deployment of two expandable portions using a single inflation port.

Figure 20:
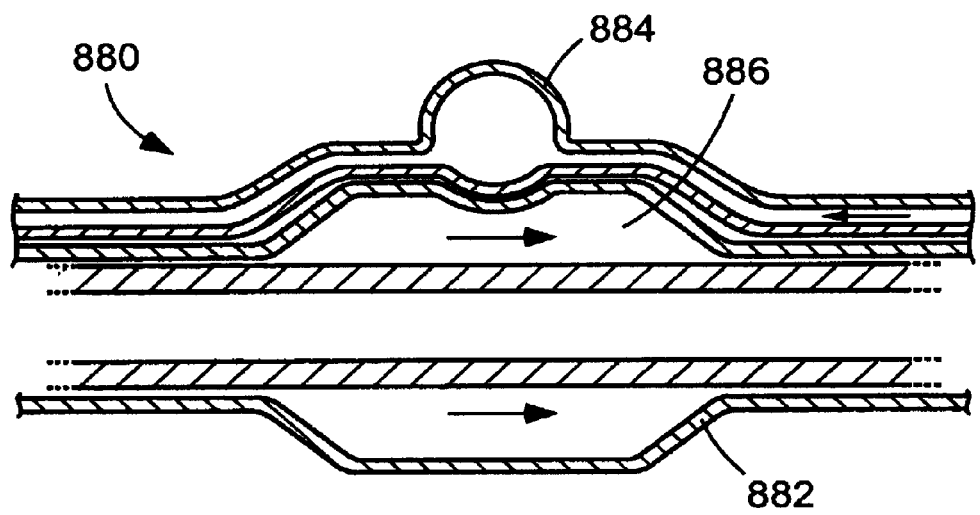
FIG. 20 is a cross-sectional view of still another embodiment of an alternative balloon construction formed according to the principles of the present invention.

Referring to FIG. 20, a cross-sectional view of an alternative embodiment of a balloon 880 is shown in an expanded state. Balloon 880 comprises a main inflatable portion 882 and an auxiliary inflatable portion 884. Main expandable portion 882 has an indentation or cavity configured and dimensioned to received a portion of auxiliary expandable portion 884 when balloon 880 is inflated. For example, as shown in FIG. 20 auxiliary inflatable portion is generally spherically shaped and when inflated, cavity 886 is aligned and positioned to accommodate a portion of the spherical shape. In this regard, when balloon 880 is inflated, the inflated balloon has the approximate peripheral shape of a cylinder with a hemispherical protrusion. In use, the auxiliary expandable portion 884 is configured to deploy or extend outwardly deployable elements of a stent into a bifurcation. In operation, when both expandable portions are inflated, such a balloon configuration allows for varying expansion capabilities and preferably prevents the region of a stent adjacent second inflatable portion 884 from over expanding into the bifurcated region. As a result, the possibility of causing trauma to the vessel is preferably limited.

While the invention has been described in conjunction with specific embodiments and examples thereof, it is evident that many alternatives, modifications and variations will be apparent to those skilled in the art upon reading the present disclosure. Accordingly, it is intended to embrace all such alternatives, modifications and variations that fall within the spirit and broad scope of the appended claims. Furthermore, features of each embodiment can be used in whole or in part in other embodiments.

What is claimed is:

1. A stent delivery system comprising:
    a catheter shaft including a proximal end portion, a distal end portion, and an inflation lumen;
    a bifurcated balloon coupled to the distal end portion of the catheter shaft and in fluid communication with the inflation lumen, the bifurcated balloon including a first balloon branch and a second balloon branch, the first balloon branch including a first inflatable portion and the second balloon branch including a second inflatable portion, the second balloon branch having a proximal end and a distal end, wherein the proximal end of the second balloon branch is directly attached to the first balloon branch proximal of a proximal end of the first inflatable portion, and wherein the distal end of the second balloon branch is directly attached to the first balloon branch distal of a distal end of the first inflatable portion;
    wherein the first and second inflatable portions each have a length extending along a longitudinal axis of the catheter shaft, wherein the length of the second inflatable portion is less than the length of the first inflatable portion.

2. The stent delivery system of claim 1, further comprising a stent disposed about the bifurcated balloon, the stent including a proximal opening, a distal opening, and a side opening including an outwardly expandable portion, wherein the side opening is aligned with the second inflatable portion, and expansion of the second inflatable portion causes the outwardly expandable portion to expand.

3. The stent delivery system of claim 1, wherein the second inflatable portion has a generally bulbous shape and is configured to extend radially away from the first inflatable portion upon inflation.

4. The stent delivery system of claim 1, wherein the second inflatable portion is generally in the form of an offset cylinder.

5. The stent delivery system of claim 1, wherein the second inflatable portion has a generally offset bulbous shape.

6. The stent delivery system of claim 1, wherein the first inflatable portion is configured to define an indentation configured to receive a portion of the second inflatable portion.

7. The stent delivery system of claim 1, wherein the catheter shaft defines a guidewire lumen extending coaxially with the first balloon branch.

8. The stent delivery system of claim 1, further comprising a side branch sheath defining a side branch guidewire lumen, the side branch sheath extending along at least a portion of the catheter shaft.

9. A stent delivery system comprising:
    a catheter including a proximal end portion and a distal end portion, the distal end portion defining a first branch and a second branch, each of the first and second branches defining an inflation lumen, the second branch having a proximal end and a distal end, each of the proximal and distal ends of the second branch being coupled to the first branch;
    a first inflatable portion coupled to the first branch and in fluid communication with the inflation lumen of the first branch; and
    a second inflatable portion coupled to the second branch and in fluid communication with the inflation lumen of the second branch, and, when inflated, the second inflatable portion being generally bulbous in shape and configured to extend radially away from the first inflatable portion, wherein a length of the second inflatable portion is less than a length of the first inflatable portion;

wherein the proximal end of the second branch is attached to the first branch adjacent a proximal end of the first inflatable portion and the distal end of the second branch is attached to the first branch adjacent a distal end of the first inflatable portion;

wherein only one of the first and second branches includes a guidewire lumen, where the guidewire lumen extends through the first or second branch and through the corresponding first or second inflatable portion, wherein the guidewire lumen is distinct from the inflation lumen of the corresponding inflatable portion.

10. The stent delivery system of claim 9, further comprising a stent disposed about the first inflatable portion and the second inflatable portion.

11. The stent delivery system of claim 10, wherein the stent defines a proximal opening, a distal opening, and a side opening including an outwardly expandable portion, wherein the side opening is aligned with the second inflatable portion, and expansion of the second inflatable portion causes the outwardly expandable portion to expand.

12. The stent delivery system of claim 9, wherein the first inflatable portion is configured to inflate simultaneously with the second inflatable portion.

13. The stent delivery system of claim 9, further comprising a side branch sheath defining a side branch guidewire lumen, the side branch sheath extending along at least a portion of the catheter.

14. The stent delivery system of claim 9, wherein the first branch and the second branch each have a longitudinal axis, the longitudinal axis of the first branch being substantially parallel to the longitudinal axis of the second branch, and wherein, when inflated, the second inflatable portion is disposed offset from the longitudinal axis of the second branch.

15. A stent delivery system, comprising:
   an elongate shaft including a proximal region, a distal region, and an inflation lumen, the elongate shaft defining a first guidewire lumen;
   a first balloon disposed about the distal region of the elongate shaft, wherein the first balloon is in fluid communication with the inflation lumen of the elongate shaft;
   a second balloon disposed adjacent the first balloon, the second balloon including a balloon body portion and a first balloon leg and a second balloon leg, the first balloon leg extending proximally from the balloon body portion and the second balloon leg extending distally from the balloon body portion, the first balloon leg having a proximal end coupled directly to the elongate shaft proximal of a proximal waist of the first balloon, and the second balloon leg having a distal end coupled directly to the elongate shaft distal of a distal waist of the first balloon, wherein the second balloon is in fluid communication with the inflation lumen via the first balloon leg and/or the second balloon leg;
   wherein the first and second balloons each have a length extending along a longitudinal axis of the elongate shaft, wherein the length of the second balloon body portion is less than the length of the first balloon.

16. The stent delivery system of claim 15, wherein the first guidewire lumen extends through the elongate shaft and the first balloon.

17. The stent delivery system of claim 15, further comprising a side branch sheath defining a side branch guidewire lumen, the side branch sheath extending along at least a portion of the elongate shaft.

18. The stent delivery system of claim 15, further comprising a stent disposed about the first balloon and the second balloon, the stent including a proximal opening, a distal opening, and a side opening including an outwardly expandable portion, wherein the side opening is aligned with the second balloon, and expansion of the second balloon causes the outwardly expandable portion to expand.

19. The stent delivery system of claim 15, wherein the second balloon has a generally bulbous shape and is configured to extend radially away from the first balloon upon inflation.

20. The stent delivery system of claim 15, wherein the second balloon has a generally offset bulbous shape.

* * * * *